United States Patent [19]

Peck

[11] Patent Number: 5,358,851
[45] Date of Patent: Oct. 25, 1994

[54] IMMUNOASSAY FOR AROMATIC RING CONTAINING COMPOUNDS

[75] Inventor: Dana P. Peck, Kennebunk, Me.

[73] Assignee: Quantix Systems, L.P., Cinnaminson, N.J.

[21] Appl. No.: 711,377

[22] Filed: Jun. 6, 1991

Related U.S. Application Data

[63] Continuation of Ser. No. 200,952, Jun. 1, 1988, abandoned, which is a continuation-in-part of Ser. No. 59,721, Jun. 9, 1987, abandoned.

[51] Int. Cl.$^5$ .................... G01N 33/53; C12Q 1/64
[52] U.S. Cl. .................. 435/7.93; 435/7.92; 435/9; 435/28; 435/188; 435/240.27; 435/961; 435/975; 436/544; 436/547; 436/548; 436/140; 530/389.8; 530/403
[58] Field of Search .............. 435/7.9, 7.91–7.95, 435/28, 188, 810, 9, 172.2, 961, 975, 240.27; 436/518, 538, 540, 544, 546–548, 800, 805–806, 815, 822, 139–140; 530/388.1, 388.9, 389.8, 403, 807; 424/85.8, 88

[56] References Cited

U.S. PATENT DOCUMENTS

| | | | |
|---|---|---|---|
| 4,208,399 | 6/1980 | Karol et al. | 436/513 X |
| 4,241,177 | 12/1980 | Singh et al. | 435/7 |
| 4,383,984 | 5/1983 | Karol et al. | 424/1 |
| 4,456,691 | 6/1984 | Stark | 436/543 |
| 4,489,157 | 12/1984 | Khanna et al. | 435/7 |
| 4,503,143 | 3/1985 | Gerber et al. | 435/7 |
| 4,594,327 | 6/1986 | Zuk | 436/514 |
| 4,596,771 | 6/1986 | Cidlowski et al. | 435/7 |
| 4,650,771 | 3/1987 | Buckler et al. | 436/536 |
| 4,900,664 | 2/1990 | Israel et al. | 436/548 |

OTHER PUBLICATIONS

Walker et al, "Monoclonal Anti-Azo Benzene Arsonate Antibodies . . ." in SCAN. J Immuno L 13 (5) 1981, 443–440 Biological Abstract Biosis No. 72080920.
Allen et al, "Development of a Monoclonal Antibody Immunoassay for the Detection of Gasoline and Diesel Fuel in the Environment" Enviroline No. 92–013940 Abstract.
Tse et al, "Induction of Murine Reagenie Antibodies by Toluene Dilgocyanate . . ." in American Review of Respiratory Disease, vol. 120, pp. 829–835, 1979 NIOSH Abstract–00136945.
Haugen et al, "Determination of Polycyclic Aromatic Hydrocarbons . . .", Cancer Research, No. 46 (1986) pp. 4178–4183.
Riad–Fahmy et al, "Radio–and Enzyme Immunoassays", *Drug Fate Metabolism*, vol. 5 (1985) pp. 51–98.
Yolken, "Enzyme Immunoassays . . .", *Review of Infectious Diseases*, vol. 4, No. 1 (1982) pp. 35–50.
Reese & Cabra, Journal of Immunology 114:863 (Feb. 1975).
DeHurtado & Osler, Proc. Soc. Exp. Biol. & Med. 149:628 (1975).
Nagao, Arerugi 34(11):1040 (1985).
Moolten, F. L. et al, Nature 272:614 (13 Apr. 1978).
Alkan, S. S. et al, Journal of Experiment Med. 136:387 (1972).
Schwartz, H. et al, Immunochemistry 6:503 (1969).
Leskowitz, S. Nature (London) 199:85 (1963).
Leskowitz, S. Journal of Experimental Med. 117:909 (1963).

*Primary Examiner*—Carol A. Spiegel
*Attorney, Agent, or Firm*—Pennie & Edmonds

[57] ABSTRACT

The present invention provides methods, reagents and kits for determining the presence of aromatic ring-containing compounds by immunoassay techniques, including enzyme, fluorescent, chemiluminescent and biosensor immunoassay, as well as radioimmunoassay. Monoclonal and polyclonal antibodies may be used in the practice of the present invention.

35 Claims, No Drawings

IMMUNOASSAY FOR AROMATIC RING CONTAINING COMPOUNDS

This application is a continuation of application Ser. No. 200,952, filed Jun. 1, 1988, now abandoned, which was a continuation-in-part of application Ser. No. 059,721, filed Jun. 9, 1987, now abandoned.

FIELD OF THE INVENTION

This invention relates to immunoassays for aromatic hydrocarbons, to reagents for and methods of carrying out such assays and to kits comprising reagents to practice such methods.

BACKGROUND OF THE INVENTION

The effects of chemicals found in the environment, both on man and animals, is of widespread concern. The history of chemical regulation in the United States is one of increasing stringency in terms of what is "acceptable" in the environment and the workplace. Fueled by an ever-expanding body of scientific knowledge, and supported by public outcry for a "clean environment," and labor and management's interest in a cleaner, safer workplace, the demand for ability to detect environmental contaminants, and aromatic hydrocarbons in particular, and to determine how much of such substances are present in the environment, is rapidly growing.

Certain aromatic hydrocarbons, e.g., benzene, toluene, and xylene, have a broad basis of application and utilization as solvents and additives. Benzene is present in the workplace in the chemical manufacturing industry as well as industries involved in industrial manufacturing of motor fuels, inks, oils, paints, plastics, and rubber. Additionally, the materials are used in manufacturing detergents, explosives, pharmaceuticals, and dye stuffs. The National Institute of Occupational Safety and Health estimates that over two million workers in the U.S. are potentially exposed to benzene, a known cause of leukemia in humans.

Furthermore, benzene is present and its uses are enhanced in unleaded fuels for automobiles equipped with catalytic converters. Thus, benzene is a persistent and notable constituent of gasoline. Gasoline is currently leaking from an existing half million or more underground storage tanks in the U.S. Hence, the ability to detect benzene in potable water by a rapid method becomes of increasing value in assessing the presence or absence of gasoline contaminants of water supplies.

Toluene and xylene are also present in the workplace and in some petroleum fuels. Many other aromatic hydrocarbons, e.g. including chlorinated derivatives of benzene, toluene and xylene, naphthalene, styrenes, etc. are found in various environmental milieus.

At present, systems for determining the presence of aromatic hydrocarbons in the workplace and the environment include gas chromatography, mass spectrophotometry and high performance liquid chromatography.

In general, these current methods for analysis require a collection of samples of air, water, soil, etc., transportation of the sample to an analytical laboratory, and an analysis by professionals using costly equipment and reagents. The results obtained must then be transmitted back to the entity that ordered the testing. This process is expensive and time-consuming.

Thus, alternative testing procedures for aromatic hydrocarbons and their derivatives which are simpler, less expensive, and adaptable to being rapidly carried out on-site are being needed.

SUMMARY OF THE INVENTION

The present invention provides methods, reagents, and kits for determining the presence of one or more aromatic hydrocarbons in a sample by immunoassay.

It has been found that antigenic haptens can be made by conjugating serum protein antigens such as serum albumin or gamma globulin to an aromatic hydrocarbon, and that these conjugates can then be injected into animals where, in a known manner, antibodies to the aromatic ring will be produced and can be harvested. These antibodies may then be utilized in a variety of immunoassay procedures to detect environmental aromatic hydrocarbons, using various known markers to label either the aromatic hydrocarbon or antibody. In some embodiments of immunoassays either an aromatic hydrocarbon or an antibody is immobilized. Both polyclonal and monoclonal antibodies can be used in the practice of the present invention. The antibodies are heterospecific in that they will bind aromatic rings, whether or not they have attached functional groups.

Immunoassay methods that can be used in the practice of the present invention to detect aromatic hydrocarbon rings in a sample include enzyme, fluorescent, chemiluminescent and biosensor immunoassay, as well as radioimmunoassay. Such assays may be heterogeneous or homogeneous.

The assays of the present invention are used to determine the presence of compounds containing the aromatic ring, such as toluene, toluidine, 2-(p-Tolyl) ethylamine, benzene, styrene, xylene, ethylbenzene, propylbenzene, or 2-methylnaphthalene, halogenated benzenes, biphenyl compounds, etc.

DETAILED DESCRIPTION OF THE INVENTION

The present invention provides immunoassays for testing a sample for the presence of aromatic hydrocarbons rings. In such immunoassays, the aromatic hydrocarbon ring (antigen)/antibody reaction can be detected by a variety of methods, using various markers to label either the antigen or antibody to permit detection of the reaction product. Furthermore, immobilization of either the antigen or antibody will facilitate detection in many cases.

Antigen/antibody assays can be generally classed into two categories, heterogeneous and homogeneous. Heterogeneous assays require separation of the bound-labelled component from the free-labelled component prior to detection of the reaction product. Homogeneous assays do not require such a separation step. The assays can further be (1) competitive, for example, where antigen competes for labelled antibody with a solid-phase antigen or where antigen competes with labelled antigen for a solid-phase antibody or (2) noncompetitive where there is a direct relationship between label and antibody or antigen.

In one embodiment of the present invention, the method of detecting the presence of at least one aromatic hydrocarbon ring in a sample comprises the steps:

(a) Forming a conjugate between (i) an immunological equivalent of the aromatic hydrocarbon ring or the aromatic hydrocarbon ring itself, and (ii) a composition capable of detection;

(b) Contacting the conjugate and the sample to be tested for the aromatic hydrocarbon ring with an antibody which reacts with the aromatic hydrocarbon ring, under conditions so that the conjugate and the aromatic hydrocarbon ring in the sample compete for binding sites on the antibody; and (c) Detecting the presence of the aromatic hydrocarbon ring by measuring the reaction of bound conjugate with a composition responsive to the composition capable of detection.

In some embodiments, the antibody is immobilized to facilitate detection.

In yet another embodiment of the present invention, the method of detecting the presence of at least one aromatic hydrocarbon ring in a sample comprises the steps of:

(a) Immobilizing the aromatic hydrocarbon ring or its immunological equivalent;

(b) Forming a conjugate between (i) an antibody which binds the aromatic hydrocarbon ring or an immunological equivalent thereof, and (ii) a composition capable of detection;

(c) Contacting the conjugate and the sample to be tested for the immobilized aromatic hydrocarbon ring with the aromatic hydrocarbon ring or immunological equivalent thereof of step (a) under conditions so that the immobilized hydrocarbon and the aromatic hydrocarbon ring in the sample compete for binding sites on the conjugate; and (d) Detecting the presence of the aromatic hydrocarbon ring by measuring the reaction of bound conjugate with a composition to which it is responsive.

Immunoassay methods that can be used in the practice of the present invention to detect the presence or absence of aromatic hydrocarbons in a sample include enzyme, fluorescent chemiluminescent and biosensor immunoassay, as well as radioimmunoassay. In enzyme-lined immunoassays (ELISA), in accordance with the present invention, the aromatic hydrocarbon ring(s) or interest can be labelled directly with an enzyme or indirectly by use of enzyme-labelled antibodies which under appropriate conditions catalyze a reaction with a substrate. The enzyme activity is typically detected by formation of a colored reaction product i.e., a colored end point that may be easily detected by eye or measured by spectroscopic or reflectance means. Several enzymes, including alkaline phosphatase, horseradish peroxidase (HRP) and glucose oxidase have been coupled to both antigen and antibody. HRP is commonly used and several substrates are available for it. For visual detection, the substrate will usually comprise a solution of a peroxide such as hydrogen peroxide and a chromogenic material such as ophenylenediamine or tetramethylbenzidine which manifests a color upon oxidation.

In fluorescent immunoassay techniques for use in the present invention, the aromatic hydrocarbon ring(s) of interest can be labelled directly with fluorochromes, or indirectly with fluorochrome-labelled antibodies. Fluorochromes are dyes that absorb radiation (e.g., ultraviolet light), are excited by it, and emit light (e.g., visible light).

The assays of the present invention are applicable to any compound containing an aromatic hydrocarbon ring that is free of steric hindrance or blockage to reaction with an antibody. Exemplary aromatic hydrocarbon rings containing compounds include toluene, toluidene, 2-(p-Tolyl) ethylamine, benzene, styrene, xylene, ethylbenzene, propylbenzene, or 2-methyl-napthalene, halogenated aromatic hydrocarbons, etc.

The amount of aromatic hydrocarbon ring detected can vary over a wide range. For example, immunoassays in accordance with the present invention can be designed by one skilled in the art to detect from about 1 part per trillion ($10^{-12}$ g) to about 1000 parts per million ($10^{-3}$ g) of aromatic hydrocarbon ring.

Monoclonal antibodies to aromatic hydrocarbon rings for use in the practice of the present invention are made using immunization and hybridoma culturing techniques well known to those in the art. Polyclonal antibodies to aromatic hydrocarbons for use in the practice of the present invention are also made using techniques known to those skilled in the art. Heterospecific antibodies are particularly useful in conducting tests of the present invention for screening purposes such as, e.g., detecting the presence of gasoline in a soil sample, because a variety of aromatic hydrocarbons are found in gasoline.

The present invention also provides a polyclonal IgG antibody preparation which binds at least one aromatic hydrocarbon ring, the antibody preparation produced by a method which comprises the steps of: (a) administering to a host a predetermined quantity of a composition comprising a hydrocarbon containing the ring or an immunological equivalent coupled to a biologically acceptable carrier protein, (b) collecting sera from the host, and (c) purifying IgG antibody from the sera. An immunological equivalent of an antigen has the ability, when introduced into a host, to cause the production of antibodies to the antigen. A heterospecific polyclonal antibody preparation, preferred in some embodiments, e.g., aromatic hydrocarbon screening tests, of the subject invention was produced by developing antibodies in rabbits against the toluene derivative, tolylacetic acid. The immunogen used consisted of tolylacetic acid molecules conjugated to Bovine Serum Albumin molecules. The resulting antibody binds toluene and also binds a number of other aromatic hydrocarbons containing the benzene ring, including, but not limited to, benzene, toluidine, 2-(p-Tolyl)ethylamine, styrene, xylene, ethylbenzene, propylbenzene and 2-methylnaphthalene.

In accordance with the present invention, the antibody or the aromatic hydrocarbon may be labelled with radioactivity, enzymes, fluorochromes or luminogens. At present, enzymes are a preferred label. Although any enzyme which can be conjugated to an antibody or an aromatic hydrocarbon can be used in assays according to the present invention, peroxidases are a preferred class of enzymes, and horseradish peroxidase is particularly preferred. The chromogen for use in enzyme immunoassays, according to the present invention, can be any chromogen that is capable of changing or producing a color in the presence of an enzyme and its substrate. 3,3',4,5'-tetramethylbenzidine (TMB) is a preferred chromogen when the enzyme used is horseradish peroxidase.

Although any suitable immunoassay technique, such as RIA, EIA, or ELISA, may be used for the detection of aromatic hydrocarbon rings, according to the present invention, a preferred immunoassay technique is a colorimetric ELISA competitive immunoassay, where the antibody is immobilized and the aromatic hydrocarbon to be detected is conjugated with an enzyme. In this type of competitive enzyme immunoassay, a predetermined number of conjugate molecules compete with an unknown number of aromatic hydrocarbon molecules in the sample for a predetermined number of binding sites on the antibody. In such colorimetric enzyme immunoassays, sufficient conjugate must be bound so that when the color formation or change occurs, the color or color change is capable of detection visually or by an appropriate instrument. Concentrations of aromatic hydrocarbons from about one part per million ($10^{-6}$ g) to about 1000 parts per million ($10^{-3}$ g) have been found useful in ELISA's of aromatic hydrocarbons according to the present invention. However, the method is suitable for any amount of aromatic hydrocarbon present as long as the color can be detected.

A programmable differential rate spectrophotometer is used in the Examples set forth below. However, the methods of the present invention can be adapted by one skilled in the art to use in other types of spectrophotometers. Similarly, the detectable reaction product is not limited to a chromophore but includes other labels as described above.

In one embodiment of the present invention, the assay matrix is a triple antibody layer. Rabbit IgG is immobilized on the inside of a polystyrene tube using techniques known to those skilled in the art, e.g., via adsorption or the glutaraldehyde method (See, e.g., T. Boenisch, Protides of Biological Fluids, 24th Colloq. (1976), p. 743, Ed. H. Peeters.). Then, using conventional techniques, goat anti-rabbit IgG is immunologically bound to the rabbit IgG, followed by the immunological binding of a rabbit antibody prepared in accordance with the present invention which reacts with the aromatic hydrocarbon ring in question.

The invention also provides kits for performing the assay of aromatic hydrocarbons. One embodiment of such a kit comprises in combination: (a) an antibody which reacts with at least one aromatic hydrocarbon ring; and (b) a conjugate of (i) an immunological equivalent of the hydrocarbon or the hydrocarbon ring itself, and (ii) a label substance capable of detection.

In such kits, wherein the detectable reaction product comprises a substance which emits radiation or produces a conductivity change, a luminogen, a fluorogen or an enzyme responsive to a chromogen, there may also be provided a composition which can react in the presence of the conjugate to produce a color, a color change, emission of light, fluorescence or a conductivity difference.

The present invention also includes a kit for carrying out an immunoassay to detect the presence of at least one aromatic hydrocarbon ring comprising in combination:

(a) an immobilized aromatic hydrocarbon or an immunological equivalent thereof; and (b) A conjugate between (i) an antibody which binds the aromatic hydrocarbon ring or which binds the immunological equivalent thereof, and (ii) a composition capable of detection.

In the kits described above, either the conjugate or antibody may be immobilized to facilitate detection. The kits may also include items such as standards, buffers and so forth.

Samples which can be tested for the presence of aromatic hydrocarbons by use of immunoassays in accordance with the present invention include, but are not limited to, particulate samples, e.g., activated charcoal, air, water and soils.

Immunoassays in accordance with the present invention can be applied to several areas where the detection and/or quantitative or semi-quantitative analysis of aromatic hydrocarbons is required. The test can be carried out on site in the industrial workplace for individual monitoring of workers exposed to hazardous substances. In this case, the aromatic hydrocarbons present in the air are adsorbed on the activated charcoal contained in a dosimeter badge. The charcoal is extracted with methanol, as described below, and assayed by an immunoassay of the present invention. Groundwater can also be assayed, and in many instances, requires no extraction step; in such cases, an aliquot of the water to be tested is simply added to the assay instead of the extraction solution. Soil or gravel samples, e.g., those known or suspected to be contaminated with gasoline or kerosene, can be extracted in the same manner as is described above for the activated charcoal.

Immunoassays, as taught therein, have several advantages over the traditional gas chromatography methods currently used. The advantages include reduced cost to assay a sample; the capability of performing on site evaluations; and shorter turn around times. Moreover, such immunoassays can be designed to be rapid (the immunoassays described below take, on the average, 10 minutes to perform).

The following examples are provided to further illustrate the invention.

EXAMPLE I—ANTIBODY PREPARATION

Materials, Methods, and Techniques

Tolylacetic Acid was covalently linked to a number of proteins including Bovine Serum Albumin (BSA) and Bovine Gamma Globulin (BGG).

Hapten BGG conjugates were used to immunize rabbits and mice.

Preparation of the N-Hydroxy Succinimide (NHS) Ester p-Tolylacetic Acid

The preparation of hapten protein conjugates requires the activation of p-Tolylacetic Acid, and the subsequent coupling of the activated hapten to the desired protein.

Tolylacetic Acid was purchased from Aldrich and used without modification or purification.

Experimental Protocol: NHS-ester of p-Tolylacetic Acid

1. The hapten (p-Tolylacetic Acid), hydroxethyl succinimide and 1-ethyl (3-dimethylaminopropyl) carbodiimide (1:1.1:1.1 molar ratio, respectively) were weighed into a flask equipped with a stir bar and vacuum dried overnight at room temperature.
2. Dimethylformamide (DMF) (dried over 4A molecular sieves) was added to the flask to obtain a 0.2 M hapten solution. The flask was stoppered and allowed to stir overnight at ambient temperature.
3. The crude NHS-ester was used in conjugations without further purification.

Conjugation of P-Tolylacetic-NHS ester to BGG and BSA

1. The activated hapten (p-Tolylacetic-NHS ester) in aliquots of 5–20 microliters (depending on reaction size) was added to a cold (ice bath) stirring solution of protein (BGG or BSA) in 0.1 M Carbonate, pH 9.5, Buffer. The protein concentration was approximately 60–100 mg/ml. The activated hapten was added slowly over a period of 1–1.5 hours to an approximate end point of 50:1 hapten: protein ratio.
2. The conjugation was monitored by withdrawing aliquots of the protein conjugation solution and determining the amine content by TNBS Titration. It is assumed that the moles of amines lost is equal to the moles of hapten bound. Reactions were usually allowed to proceed 30 minutes past the last hapten addition.
3. The crude conjugates were purified by chromatography on a SEPHADEX G-25 column in 0.1 M Carbonate (pH 8.5) Buffer, dialyzed against four changes of distilled water, and lyophilized. A small aliquot of the chromatographed protein is saved to determine the hapten number.
4. The hapten number was determined by amine content by Trinitrobenezine Sulfonate (TNBS) Titration of the protein sample before and after conjugation. The protein concentrations are determined by UV and/or the Lowry Protein Method.

The hapten numbers of the conjugates prepared are given below:

| CONJUGATE | HAPTEN NUMBER | PROTEIN YIELD |
|---|---|---|
| p-Tolylacetic BGG | 44.5 | 340 mg |
| p-Tolylacetic BSA | 32 | 190 mg |

Animal Programs

Animal immunization programs with three rabbits and ten mice were initiated with p-Tolylacetic BGG conjugates. The initial injections were prepared with Complete Freunds' Adjuvant while subsequent injections (boost) were prepared with Incomplete Freunds' Adjuvant.

Immunization and Bleeding

1. New Zealand White Rabbits, with approximate weights of 7–8 pounds per animal, were used in the immunization program.
2. 2.5 mg/ml of the antigen was injected into each animal per month (3–4 weeks).
3. Test bleeds of 7–10 milliliters of blood were obtained each month or 7–10 days following immunization.
4. The serum was separated from the blood using the following procedure:
   blood was drawn from the ear vein and allowed to stand at room temperature for one hour.
   The sample was cooled to 4° C. (refrigerated) for four hours to clot, and centrifuged to separate the cells from the serum.
   The serum was separated from the clot and centrifuged again at high speed to remove lipids.
5. The animal sera was screened for presence of specific antibodies by ouchterlony immunodiffusion analysis using the BSA hapten conjugate as the antigen.
6. Antisera which gave a positive response to ouchterlony immunodiffusion analysis were evaluated for inhibition in competitive solid phase EIA, using conventional techniques.
7. Production bleeds of 40–50 milliliters of animal blood (18–23 ml serum) were obtained in the same manner as test bleeds.

Injections

The injections containing the immunogens are prepared one to three days prior to use. The lyophilized immunogen is dissolved in saline. An equal volume of adjuvant (Freunds' Complete for the initial immunization and Freunds' Incomplete for subsequent boost) and immunogen-saline mixture is combined and emulsified. One milliliter of the emulsion containing 2.5 mg of the immunogen is injected beneath the skin of the rabbit. The animals were bled 7–10 days following immunization.

EXAMPLE 2—COMPETITIVE ENZYME IMMUNOASSAY REAGENT AND PROCEDURE

Assay Principle

The test described below is a competitive enzyme immunoassay in which a fixed number of enzyme-labelled antigen molecules compete with an unknown number of antigen molecules in the sample for a fixed number of binding sites on antibodies directed against the antigen. As the number of antigen molecules in the sample increases, the number of bound labelled antigen molecules decreases due to competition. Ergo, after the unbound antigen (labelled and unlabelled) is removed and substrate and chromogen are added, the degree of color development will depend on how much labelled antigen remains immunologically bound. The greater the concentration of antigen in the sample, the less labelled antigen bound after separation and the lower the rate of color development. A programmable, differential rate spectrophotometer which references the rate of color development in the sample against a calibrator (designed reference) containing a fixed mass of antigen was used in carrying out the assays described below.

Preparation of Assay Matrix

The assay matrix is a triple antibody layer comprising rabbit IgG (Pel-Freeze), anti-rabbit IgG (Pel-Freeze) and primary antibody (prepared in accordance with Example 1 above) in a 12×75 mm polystyrene tube. Rabbit IgG was bound to the inside of the polystyrene tube via the glutaraldehyde method (See, e.g., Boenisch, supra.).

The following steps immunologically bind the second and the primary antibody resulting in a triple layer. A 1:500 dilution of Goat anti-Rabbit serum (Pel-Freeze) was made with 10 mM phosphate buffer, 0.15 M phosphate-buffered saline (PBS) of pH 7.5 to which 1 mg/ml Bovine Serum Albumin (BSA) is added (PBS-BSA). Six hundred microliters of this solution was pipetted into tubes and incubated overnight at room temperature. Then the tubes were rinsed 1× with deionized water. A 1:20,000 dilution of the primary antibody was prepared in PBS-BSA and six hundred microliter aliquots were added to the tubes. The tubes were incubated, aspirated, rinsed, and placed in a drying room for about 24 hours. The tubes are subsequently stored at 4° C.

The primary antibody was developed in rabbits against the toluene derivative para-tolylacetic acid conjugated to BSA or BGG as described in Example 1 above. The resulting antibodies react with several compounds all containing the aromatic ring; toluene, toluidine, 2-(p-Tolyl)ethylamine, benzene, styrene, xylene, ethylbenzene, propylbenzene, 2-methyl-naphthalene, for example.

Aromatic Hydrocarbon - HRP Conjugate

Reference and Sample

Tolylacetic acid molecules were conjugated to the enzyme Horseradish Peroxidase using methods known to those skilled in the art. See, e.g., Enzyme Labelling of Antibodies, J. of Immunoassay, Vol. 4, No. 3, 1983, First Edition, E. Ishikawa. The resultant conjugate was diluted in a protein medium consisting of 50% fetal calf serum, 0.5 M Trizma Base, with conventional antimicrobial agents, and 0.05% surfactant, about pH 7.0.

Two vials of conjugate are required for conducting a single test when using a differential rate spectrophotometer, as described above. In one such vial, a predetermined quantity of the conjugate and of tolylacetic acid is present which gives the same test response as a certain mass of the aromatic ring-containing compound(s) to be detected (or combined benzene, toluene, and xylene-referred to as BTX). 35 mg of p-tolylacetic acid which has been determined to give the same response (absorbance after a set time) as 21 mg of Toluene (or combined BTX). This vial is designated as the Reference or 'R' vial. The other vial containing the predetermined quantity of conjugate but no tolylacetic acid is labelled 'S' for Sample. These materials are then lyophilized and stoppered under vacuum.

RUNNING THE TEST

One 'R' vial and one 'S' vial are placed in a tray. A predetermined quantity of a dissolving solution comprising 0.09% TRIS buffer and 0.025% detergent, e.g., Brij-35 is used to dissolve the freeze-dried materials.

If the material to be tested for the presence of aromatic ring containing compound(s) requires extraction as from, e.g., activated charcoal, it is extracted by shaking it in a small container with a predetermined volume of methanol. A measured quantity of the methanol extract is placed in the 'S' vial. The same volume of pure methanol is placed in the 'R' vial to compensate for any effects of methanol in the 'S' vial. The entire contents of the 'R' and 'S' vials are transferred to the 'R' and 'S' antibody-coated tubes, respectively.

The reaction mixture is incubated for about 5 minutes followed by 5 forceful rinses with water. Six drops, about 250 ml, of chromogen (3,3',5,5'-Tetramethylbenzidine; 40% methanol; 20% glycerol) are added to each tube. Then quickly and accurately the volume in each tube is brought up to a volume of between 500–600 microliters with the substrate solution, a 0.04% urea peroxide, 0.09% M sodium acetate, 0.1 M citric acid, pH 5.0.

After swirling and tapping the color tube development is monitored by means of a computer-linked Differential Rate Spectrophotometer, as described above.

An intermittent mixing device was built into the spectrophotometer using conventional techniques in order to assure accurate absorbance readings (color development is more rapid on the bottom of the tube where the surface area is greater). Absorbance readings are taken every 20 seconds (a few seconds after the mixing stops) and the readings are stored in the computer linked to the spectrophotometer. The first six readings are ignored. Calculations are the performed based on the equation $(100+K)(r)-K=ppm$ (g per ml), where K is a constant determined from experimental data and r is the ratio:

$$r = \frac{\text{Absorbance Change/Change in time (Reference)}}{\text{Absorbance Change/Change in time (Sample)}}$$

A mean of about nine such calculations was computed and shown on the liquid crystal display of the linked computer. A printer may also be attached to the spectrophotometer for a hard copy of data. Since calculations are based on the ratio of the rate of color development of the reference against the rate of color development of the sample, many factors which affect the assay, such as temperature and increased incubation time do not affect the result of the assay; both the reference and the sample should be affected equally by these factors.

EXAMPLE 3—ANTIBODY/AROMATIC HYDROCARBON BINDING

The reactivity of an antibody prepared in accordance with Example 1, above, with various aromatic hydrocarbons was determined using the general procedure outlined in Example 2, above.

Preparation of Standards

All standards were made with methanol (reagent grade) by making serial dilutions of the pure chemical to be tested. If the substance was in crystalline form, a weight/volume method was used. If the compound was a liquid, the relationship—density of the compound X $10^6$ parts per million (microgram per ml) was used to determine the actual mass. Subsequent serial dilutions were then made until a desired concentration (microgram per ml or ppm) was achieved.

Assay Steps a) 250 ml of the Universal diluent is pipetted into each of from about 6 to about 10 triple-layer anti-tolyl coated polystyrene tubes and one uncoated polystyrene tube (to check for nonspecific binding-NSB).

b) 150 ml of dissolving solution as described in Example 2 above was added to each tube.

c) 50 ml of a working dilution of tolylacetic-HRP conjugate was added to the tubes. The working dilution of the conjugate for these particular tests varied, but the dilution is noted in the tabulation provided below.

d) 100 ml of 100% methanol was pipetted into one-half of the reference tubes and the NSB tubes. This represented the zero dose or the maximum binding (i.e., maximum color development). Into the other tubes, 100 1 was pipetted of a standard solution containing the aromatic hydrocarbon to be tested for cross-reactivity.

e) The tubes are capped (a precaution since the aromatics are hydrophobic and the assay mixture is aqueous based) and incubated for 5 minutes.

f) After the 5 minute incubation, the solutions were decanted, and the tubes were rinsed 5× forcefully with a squeeze bottle.

g) The water was shaken out of the tubes thoroughly. Equal volumes of substrate and chromogen were added to a glass vial, vortexed, and 500 1 of the mixture was added to each tube quickly.

h) Color was allowed to develop from about 5 to about 10 minutes until the reaction was terminated with 1 ml of $1NH_2SO_4$, switching the color from blue to yellow. The tubes were then read at 450 nm.

The aromatic hydrocarbons listed below were tested for reactivity with an antibody preparation made in accordance with Example 1 above. The test procedures and volumes were essentially as described above.

The following aromatic hydrocarbons were determined to react with the antibody: Benzene, Xylene, Toluene, Styrene, Toluidine, 2-(p-Tolyl)ethylamine, Ethylbenzene, 2-Methyl-naphthalene, and Propyl-benzene.

EXAMPLE 4

Correlation with Gas Chromatography analysis

Samples comprising a mixture of aromatic hydrocarbons were analyzed using the general procedures outline in Example 2, above, as well as by conventional gas chromatography techniques, to determine the presence of such aromatic hydrocarbons. The analysis using the immunoassay procedures of Example 2 has been determined by regression analysis, a technique well-known to those skilled in the art, to correlate well with the analysis using conventional gas chromatography techniques. The correlation coefficient was determined to be 0.989.

The samples used in the regression analysis consisted of (i) serial dilutions of gasoline and (ii) soil samples, including gravel and clay, which were spiked with gasoline and then extracted with methanol as described in the above examples.

The antibody preparation used in the regression analysis was prepared in accordance with Example 1 above.

EXAMPLE 5—MONOCLONAL ANTIBODY PREPARATION

Monoclonal antibodies are prepared according to the classical method of Kohler & Milstein by injecting an immunogen such as tolylacetic acid bound to BSA into a mouse spleen. After two to three weeks, the mouse is sacrificed, the spleen is removed and digested and the lymphocyte cells are extracted. A selection process involving the screening of the lymphocytes for antibody activity on microtiter plates is carried out as taught by Kohler & Milstein. The lymphocytes selected in the screening process are then each fused with a mouse myeloma cell to form a hybridoma. Each hybridoma is then injected into the stomach of a mouse. Each injected mouse is sacrificed approximately 2 weeks later and the ascites fluid produced by its stomach in the interim is recovered. From each separate batch of ascites fluid a different monoclonal antibody capable of bind aromatic ring-containing compounds is recovered.

The examples, using solid-phase, enzyme-linked competitive immunoassay, are merely one example of the use of the present invention. Variations in the actual process described in the examples will be apparent to those skilled in the art.

Therefore, the present invention is to be considered as limited only by the appended claims.

What is claimed is:

1. An antibody useful in an immunoassay of a sample to determine the presence or amount of an aromatic ring-containing containing compound derivable from petroleum or a petroleum product, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene.

2. The antibody according to claim 1, wherein said antibody specifically binds to toluene, benzene, styrene, xylene, ethylbenzene, propylbenzene and 2-methylnaphthalene.

3. The antibody according to claim 1 or 2, wherein said antibody is capable of detecting an aromatic ring-containing compound selected from the group consisting of benzene, 2-(p-tolyl)-ethylamine, toluene, toluidine, styrene, xylene, ethylbenzene, propylbenzene and 2-methylnaphthalene at a concentration from about 1 part per trillion to about 1000 parts per million of said sample in said immunoassay.

4. A method for determining the presence or amount of an analyte in a sample, wherein the analyte is an aromatic ring-containing compound derivable from petroleum or a petroleum product and selected from the group consisting of benzene, 2-(p-tolyl)-ethylamine, toluene, toluidine, styrene, xylene, ethylbenzene, propylbenzene and 2-methylnaphthalene, which method comprises the steps of:
   (a) contacting the sample with
      (i) a predetermined amount of conjugate comprising a detectable label conjugated to p-tolylacetic acid, and
      (ii) a predetermined amount of an antibody, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene, under conditions in which the analyte in the sample competes with the predetermined amount of conjugate for specific binding sites on the predetermined amount of antibody; and
   (b) determining the specific binding of the conjugate to the antibody by measuring the amount of the label specifically bound to the antibody, wherein the amount of label specifically bound to the antibody is inversely proportional to the amount of the analyte present in the sample.

5. The method of claim 4 wherein the antibody specifically binds to toluene, benzene, styrene, xylene, ethylbenzene, propylbenzene and 2-methylnaphthalene.

6. The method of claim 4 wherein the antibody is immobilized on a solid phase matrix.

7. The method of claim 4 wherein the determining step (b) is performed by measuring color, a color change, rate of color change, light emission, fluorescence, radiation, or a difference in conductivity.

8. The method of claim 4 wherein the detectable label is an enzyme and the determining step (b) is performed by measuring a colored product produced by the enzyme acting on a chromogenic substrate therefore.

9. The method of claim 8 wherein the enzyme is horseradish peroxidase and the chromogenic substrate is 3,3',5,5=-tetramethyl benzidine.

10. A method for determining the presence or amount of an analyte in a sample, wherein the analyte is an aromatic ring-containing compound derivable from petroleum or a petroleum product and selected from the group consisting of benzene, 2-(p-tolyl)-ethylamine, toluene, toluidine, styrene, xylene, ethylbenzene, propylbenzene and 2-methylnaphthalene, which method comprises the steps of:
   (a) contacting the sample with (i) a solid phase matrix having immobilized thereon a predetermined amount of p-tolylacetic acid molecules, and (ii) a predetermined amount of conjugate comprising a detectable label conjugated to an antibody, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene, under conditions in which the immobilized p-tolylacetic acid competes with the analyte in the sample for specific binding sites on the antibody portion of the predetermined amount of the conjugate; and (b) determining the specific binding of the conjugate to the immobilized ptolylacetic acid by measuring the amount of the label specifically bound to the solid phase matrix, wherein the amount of label specifically bound to the solid phase matrix is inversely proportional to the amount of the analyte present in the sample.

11. The method of claim 10 wherein the antibody specifically binds to toluene, benzene, styrene, xylene, ethylbenzene, propylbenzene and 2-methylnaphthalene.

12. The method of claim 10 wherein the determining step (b) is performed by measuring color, a color change, rate of color change, light emission, fluorescence, radiation, or a difference in conductivity.

13. The method of claim 10 wherein the detectable label is an enzyme and the determining step (b) is performed by measuring a colored product produced by the enzyme acting on a chromogenic substrate therefore.

14. The method of claim 10 wherein the enzyme is horseradish peroxidase and the chromogenic substrate is 3,3',5,5'-tetramethyl benzidine.

15. A method for determining the presence or amount of an analyte in a sample, wherein the analyte is an aromatic ring-containing compound derivable from petroleum or a petroleum product and selected from the group consisting of benzene, 2-(p-tolyl)-ethylamine, toluene, toluidine, styrene, xylene, ethylbenzene, propylbenzene and 2-methylnaphthalene which specifically binds to an antibody, which method comprises the steps of:

(a) producing said antibody by immunizing an animal with p-tolylacetic acid conjugated to an immunogenic carrier protein, wherein said antibody (I) is a polyclonal antibody and (II) specifically binds to the aromatic ring of benzene and to an aromatic ring of one or more compound selected from the group consisting of 2-(p-tolyl)-ethylamine, toluene, toluidine, styrene, xylene, ethylbenzene, propylbenzene and 2-methylnaphthalene;

(b) contacting the sample with (i) a predetermined amount of conjugate comprising a detectable label conjugated to the antibody produced in step (a) and a solid phase matrix having immobilized thereon a predetermined amount of p-tolylacetic acid to form specific binding complexes, or (ii) a predetermined amount of conjugate comprising a detectable label conjugated to p-tolylacetic acid and a predetermined amount of the antibody produced in step (a) to form specific binding complexes; and (c) determining the amount of label in the specific binding complexes in order to determine the amount of the analyte present in the sample.

16. The method of claim 15 wherein the antibody specifically binds toluene, benzene, styrene, xylene, ethylbenzene, proplylbenzene and 2-methylnaphthalene.

17. The method of claim 4, 10 or 15 wherein the sample is a substance suspected of being contaminated with a petroleum product selected from the group consisting of gasoline, kerosene and fuel oil.

18. A method for determining the presence or amount of gasoline in an environmental sample, comprising:

(a) contacting the sample or an extract thereof with (i) a predetermined amount of conjugate comprising a detectable label conjugated to p-tolylacetic acid, and (ii) a predetermined amount of an antibody, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene, under conditions in which any gasoline in the sample competes with the predetermined amount of conjugate for specific binding sites on the predetermined amount of antibody; and (b) determining the specific binding of the conjugate to the antibody by measuring the amount of the label specifically bound to the antibody, wherein the amount of label specifically bound to the antibody is inversely proportional to the amount of the gasoline present in the sample.

19. The method of claim 18 wherein the conjugate of step (a)(i) comprises p-tolylacetic acid conjugated to a horseradish peroxidase label, the antibody is immobilized on latex particles, and the determining step (b) is performed by reacting the horseradish peroxidase with 3,3+,5,5'-tetramethyl benzidine to form a colored product indicative of the amount of the gasoline present in the sample.

20. A method for determining the presence or amount of gasoline in an environmental sample, comprising:

(a) contacting the sample or an extract thereof with (i) a solid phase matrix having immobilized thereon a predetermined amount of p-tolylacetic acid, and (ii) a predetermined amount of conjugate comprising a detectable label conjugated to an antibody, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene, under conditions in which the immobilized p-tolylacetic acid competes with any gasoline in the sample for specific binding sites on the antibody portion of the predetermined amount of conjugate; and (b) determining the specific binding of the conjugate to the immobilized p-tolylacetic acid by measuring the amount of the label specifically bound to the solid phase matrix, wherein the amount of label specifically bound to the solid phase matrix is inversely proportional to the amount of the gasoline in the sample.

21. The method of claim 20 wherein the antibody is conjugated to a horseradish peroxidase label, and the determining step (b) is performed by reacting the horseradish peroxidase with 3,3',5,5'-tetramethylbenzidine to form a colored product indicative of the amount of the gasoline present in the sample.

22. The method of claim 18 or 20 wherein the antibody specifically binds to toluene, benzene, styrene, xylene, ethylbenzene, propylbenzene and 2-methylnaphthalene.

23. The method of any of claim 18 and 21 wherein the environmental sample is water or soil.

24. The method of claim 22 wherein the environmental sample is water or soil.

25. A kit useful for an immunoassay of a sample to determine the presence or amount of at least one aromatic ring-containing analyte selected from the group consisting of 2-(p-tolyl)-ethylamine, toluene, toluidine, benzene, styrene, xylene, ethylbenzene, propylbenzene and 2-methylnaphthalene, wherein the kit comprises in combination in one or more containers:

(a) a conjugate comprising a detectable label conjugate to p-tolylacetic acid, and (b) an antibody, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene.

26. The kit of claim 25 wherein the detectable label is a label detectable by measuring color, a color change, rate of color change, light emission, fluorescence, radiation, or a difference in conductivity.

27. The kit of claim 25 wherein the antibody is immobilized on a solid phase matrix.

28. A kit useful for an immunoassay of a sample to determine the presence or amount of at least on aromatic ring-containing analyte selected from the group consisting of 2-(p-tolyl)-ethylamine, toluene, toluidine, benzene, styrene, xylene, ethylbenzene, propylbenzene, and 2-methylnaphthalene, wherein the kit comprises in combination in one or more containers:

(a) the aromatic ring-containing analyte or p-tolylacetic acid, and (b) a conjugate comprising a detectable label conjugated to an antibody, wherein said antibody (I) is a polyclonal antibody produced by immunizing an animal with p-tolylacetic acid conjugated to an immunogenic carrier protein and (II) specifically binds to the aromatic ring of benzene and to an aromatic ring of one or more compounds selected from the group consisting of 2-(p-tolyl)-ethylamine, toluene, toluidine, styrene, xylene, ethylbenzene, propylbenzene and 2-methylnaphthalene.

29. The kit of claim 28 wherein the detectable label is a label detectable by measuring color, a color change, rate of color change, light emission, fluorescence, radiation, or a difference in conductivity.

30. The kit of claim 25 or 28 wherein the detectable label is an enzyme.

31. The kit of claim 30 wherein the detectable label is horseradish peroxidase.

32. The kit of claim 25 or 28 wherein the antibody specifically binds to toluene, benzene, styrene, xylene, ethylbenzene, propylbenzene and 2-methylnaphthalene.

33. An immunogenic composition useful for producing a polyclonal antibody which specifically binds to the aromatic ring of benzene and to an aromatic ring of one or more compounds selected from the group consisting of 2-(p-tolyl)ethylamine, toluene, toluidine, styrene, xylene, ethylbenzene, propylbenzene and 2-methylnaphthalene, wherein the composition comprises p-tolylacetic acid conjugated to an immunogenic carrier protein.

34. The composition of claim 33 wherein the immunogenic carrier protein is bovine serum albumin or bovine gamma globulin, and the p-tolylacetic acid is conjugated to the immunogenic carrier protein through an N-hydroxysuccinimide linker.

35. The composition of claim 33 wherein the antibody specifically binds to toluene, benzene, styrene, xylene, ethylbenzene, propylbenzene and 2-methylnaphthalene.

* * * * *